United States Patent [19]

Ghelardoni et al.

[11] 3,968,145

[45] July 6, 1976

[54] METHYL 2(1 CHLORONAPHTH-2-YLOXY)PROPIONATE

[75] Inventors: Mario Ghelardoni; Vittorio Pestellini, both of Florence; Giovanna Volterra, Sesto Fiorentino; Nicola Pisanti, Florence, all of Italy

[73] Assignee: A. Menarini S.A.S., Italy

[22] Filed: May 13, 1974

[21] Appl. No.: 469,552

Related U.S. Application Data

[63] Continuation-in-part of Ser. No. 297,832, Oct. 16, 1972, abandoned.

[30] Foreign Application Priority Data

Oct. 21, 1971   Italy ................................. 9731/71

[52] U.S. Cl. ..................... 260/473 F; 260/500.5 H; 260/507 R; 260/520 E; 260/559 B; 424/308; 424/324

[51] Int. Cl.² ......................................... C07C 69/76

[58] Field of Search ................................ 260/473 F

[56]        References Cited

UNITED STATES PATENTS

| 3,641,134 | 2/1972 | Shen et al. ...................... 260/473 F |
| 3,740,437 | 6/1973 | Harrison et al. ................. 260/473 F |

*Primary Examiner*—Paul J. Killos
*Attorney, Agent, or Firm*—McGlew and Tuttle

[57]            ABSTRACT

This invention relates to the use of 2-(1-chloro-2-yloxy) propionic acid and its derivatives having physiological activity, notably as antiphlogistics, analgesics, analgesics and anti-pyretics. The physiologically active compounds include esters and amides of the substituted propionic acid. The compounds can be presented in conventional pharmaceutical form, including the non-toxic, pharmaceutically acceptable salts thereof.

1 Claim, No Drawings

METHYL 2(1 CHLORONAPHTH-2-YLOXY)PROPIONATE

CROSS REFERENCE TO RELATED APPLICATION

This application is a continuation-in-part of copending application Ser. No. 297,832, filed Oct. 16, 1972 now abandoned

BACKGROUND OF THE INVENTION

1. Field of the Invention

This invention relates to 2-(1-chloro-2-yloxy) propionic acid and its derivative compounds having physiological activity having uses as antipyretic, antiphlogistic and analgesic properties in pharmaceutically useful compositions.

2. Prior Art

U.S. Pat. No. 3,740,437 discloses that naphthyloxyacetic acids are useful as anti-inflammatory, analgesic and antipyretic agents. There are no propionic acid esters of the formula I disclosed therein, nor is there a specific teaching of the superiority of such esters in terms of analgesic or antipyretic activity, or antiphlogistic activity.

SUMMARY OF THE INVENTION

According to the present invention the pharmaceutically useful compositions are prepared from compounds of the formula

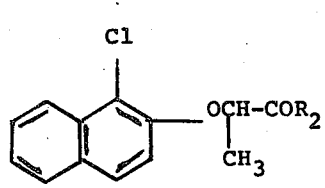

in which $R_2$ represents a hydroxy group, an alkoxy group containing from 1 to 4 carbon atoms, an aralkoxy group, an oxypropylsulfonic acid group and salts thereof, a primary amino, mono-$(C_{1-4})$-alkylamino or di-$(C_{1-4})$-alkylamino group, or a hydroxyamino group. These compounds are useful as antiphlogistic, analgesic or antipyretic agents.

Examples of preferred compounds are those wherein $R_2$ is either a methoxy, ethoxy, n-propoxy, n-butoxy or benzyloxy group.

Particularly preferred pharmaceutical compositions are prepared using compounds of formula I by virtue of the good antiphlogistic, analgesic or antipyretic activities of said compounds which include the following:

(1) methyl 2-(1-chloronaphth-2-yloxy)propionate ($R_2=CH_3O$) (b.p. 155°–137°C/0.4 mm.Hg);
(2) ethyl 2-(1-chloronaphth-2-yloxy)propionate ($R_2=C_2H_5O$) (b.p. 162°–164°C/0.4 mm.Hg.);
(3) n-propyl 2-(chloronaphth-2-yloxy)propionate ($R_2=n-C_3H_7O$) (b.p. 168°–170°C/0.4 mm.Hg.);
(4) n-butyl 2-(1-chloronaphth-2-yloxy)propionate ($R_2=n-C_4H_9O$) (b.p. 178°–180°C/0.3 mm.Hg.);
(5) sodium 3-[1-(1-chloronoaphth-2-yloxy)-ethylcarbonyloxy] propyl sulfonate ($R_2=O(CH_2)_3SO_3Na$) (m.p. 187°–189°C, decomposition);
(6) benzyl 2-(1-chloronaphth-2-yloxy)propionate ($R_2=C_6H_5CH_2O$) (b.p. 168°–170°C/0.4 mm.Hg.);
(7) 2-(1-chloronaphth-2-yloxy)propionamide, ($R_2=NH_2$) (m.p. 179°–181°C);
(8) 2-(1-chloronaphth-2-yloxy)propionylhydroxamic acid, ($R_2=NHOH$) (m.p. 155°–156°C).

Compounds of formula I show interesting physiological activities and they are useful in therapy, in particular as antiphlogistic, analgesic and antipyretic agents.

Antiphlogistic activity of various compounds of formula I were tested on carrageen-induced planter oedemas in the rat according to the method of A. C. Winter, E. A. Risely, (see G. W. Nuss, Proc. Soc. Exp. Biol. Med., 111, 544, 1962) and analgesic activity of the same compounds was estimated using phenylquinone in the mouse according to the method of E. Sigmund et al as modified by N. Pisanti, G. Volterra, (see Boll. Chim. Farm., 107, 769, 1968). In general the compounds were administered orally. They were compared with aminophenazone.

TABLE

| Compound | Antiphlogistic Activity | Analgesic Activity (°) |
|---|---|---|
| Aminophenazone | 1 | 1 |
| 2-(1-chloronaph-2-yloxy) propionic acid | 2.56 | 2.20 |
| 1 | 5.12 | 2.19 |
| 2 | 3.59 | 2.19 |
| 3 | 3.88 | 1.01 |
| 4 | 3.50 | 1.06 |
| 5 (∞) | 2.69 (∞) | 1.13 (∞) |
| 6 | 4.36 | 1.01 |
| 7 | 0.87 | 1.28 |
| 8 | 3.21 | 1.10 |

(°) The analgesic activities of formula I reported in the table lasted 1–2 hours longer than that of aminophenazone.
(∞) Administered subcutaneously.

The present invention further provides pharmaceutical compositions comprising at least one compound of formula I in association with a pharmaceutical carrier or excipient.

The pharmaceutical compositions may be presented in a form suitable, for example, for oral or parenteral administration. Examples of suitable forms of administration include, tablets, coated tablets, capsules, lozenges, dispersible powders, syrups and elixers. Preferably the compositions are presented in dosage unit form.

Compounds of formula I (as hereinbefore defined) are in general new, and per se form a feature of the present invention.

What is claimed is:

1. Methyl 2(1-chloronaphth-2-yloxy) propionate.

* * * * *